US008455546B2

(12) United States Patent
Ogihara et al.

(10) Patent No.: US 8,455,546 B2
(45) Date of Patent: Jun. 4, 2013

(54) MEDICAMENT HAVING PROMOTING ACTION ON HEPATOCYTE PROLIFERATION

(75) Inventors: Masahiko Ogihara, Tokyo (JP); Mitsutoshi Kimura, Saitama (JP); Naoto Ishibashi, Saitama (JP); Jun Kojima, Saitama (JP)

(73) Assignees: Josai University Educational Corporation, Saitama (JP); Kowa Company, Ltd., Aichi (JP)

( * ) Notice: Subject to any disclaimer, the term of this patent is extended or adjusted under 35 U.S.C. 154(b) by 0 days.

(21) Appl. No.: 13/464,432

(22) Filed: May 4, 2012

(65) Prior Publication Data

US 2012/0220659 A1 Aug. 30, 2012

Related U.S. Application Data

(62) Division of application No. 12/665,342, filed as application No. PCT/JP2008/001606 on Jun. 20, 2008, now abandoned.

(30) Foreign Application Priority Data

Jun. 21, 2007 (JP) ................................. 2007-163355

(51) Int. Cl.
*A01N 37/00* (2006.01)
(52) U.S. Cl.
USPC ............ 514/557; 514/560; 514/866; 562/598
(58) Field of Classification Search
USPC ............................ 514/557, 560, 866; 562/598
See application file for complete search history.

(56) References Cited

U.S. PATENT DOCUMENTS

| | | | |
|---|---|---|---|
| 5,580,903 | A | 12/1996 | Mawatari et al. |
| 5,916,921 | A | 6/1999 | Nishihira et al. |
| 7,547,730 | B2 | 6/2009 | Shidoji et al. |
| 2002/0119181 | A1 | 8/2002 | Muszynska |
| 2005/0250671 | A1 | 11/2005 | Shidoji et al. |
| 2006/0063838 | A1 | 3/2006 | Shidoji et al. |
| 2006/0094784 | A1 | 5/2006 | Kagawa et al. |
| 2008/0021105 | A1 | 1/2008 | Nagai et al. |
| 2009/0069424 | A1 | 3/2009 | Kagawa et al. |
| 2009/0264529 | A1 | 10/2009 | Shidoji et al. |

FOREIGN PATENT DOCUMENTS

| | | |
|---|---|---|
| JP | 63-32058 | 11/1981 |
| JP | 5-229940 | 9/1993 |
| JP | 8-67628 | 3/1996 |
| JP | 2003-252792 | 9/2003 |
| JP | 2007-23002 | 2/2007 |
| JP | 2007-45721 | 2/2007 |
| WO | 2005/079783 | 9/2005 |

OTHER PUBLICATIONS

Muto et al, N. Engl. J. Med, 1996, 334, 1561-1567.*
Wilkening et al., The American Society for Pharmacology and Experimental Therapeutics, 31, pp. 1035-1042, 2003.
Greenbaum, Cancer Biology & Therapy, 3, pp. 1200-1207, 2004.
Nakamura et al., J. Biochem. 94, pp. 1029-1035, 1983.
Kimura et al., J. Pharmacol. Sci., 115, pp. 390-398, 2011.
Nakamura et al., Biochem. Biophys. Res. Commun , 207, pp. 382-388, 1995.
Makoto Murata et al., "Polyprenoic . . . Kansuru Kenkyu", Acta Hepatologica Japonica, p. 605-612, 1985.
M. Okuno et al.; "Inhibitory Effect of Acyclic Retinoid (Polyprenoic Acid) on the Secretion of α-Fetoprotein in CCL4-Treated Rats"; J. Nut Sci. Vitaminol, 1990, p. 437-446.
T. Nakamura et al., Biohem. Biophys. Res. Commun , 133, pp. 1042-1050, 1985.
J. Mead et al., Proc. Natl. Acad. Sci. USA, 86, pp. 1558-1562, 1989.
K.S. Koch et al., Cell, 18, pp. 153-163, 1979.
M. Kimura et al., Eur. J. Pharmacol., 510, pp. 167-180, 2005.
Kanzo (Liver, Journal of the Japan Society of Hepatology), 44, pp. 383-394, 2003.
Y. Muto et al., N. Eng. J. Med., 334, pp. 1561-1567, 1996.
N. Nakamura et al., Biohem. Biophys. Res. Commun , 219, pp. 100-104, 1996.
Y. Shidoji et al., J. Lipid Res. 45, pp. 1092-1103, 2004.
D.M. Prescott, Methods in Cell Biology, 13, Chpt 4., pp. 29-83, 1976.
G. Higgins et al., Arch. Pathol.,12, pp. 186-202, 1931.
English and Japanese version of International Preliminary Report on Patentability and Written Opinion for International Application PCT/JP2008/001606.
English and Japanese version of International Search Report for International Application PCT/JP2008/001606.
Sasaki et al., "Inhibitory Effects of Polyprenoic-Acid E-5166 on Production and Secretion of Alpha Fetoprotein and Cells Kinetics in Human Hepatoma Cells," Database Biosis [Online] Biosciences Information Service, Philadelphia, PA, US, 1986, XP009138007, Database accession No. PREV198682015394 & Japanese Journal of Cancer Research, vol. 77, No. 3, 1986, pp. 264-269, ISSN: 0910-5050, Mar. 1986.

(Continued)

*Primary Examiner* — Leslie A. Royds Draper
*Assistant Examiner* — Ibrahim D Bori
(74) *Attorney, Agent, or Firm* — Greenblum & Bernstein, P.L.C.

(57) ABSTRACT

A medicament for promoting proliferation of hepatocytes and liver regeneration, which comprises a polyprenyl compound such as 3,7,11,15-tetramethyl-2,4,6,10,14-hexadecapentaenoic acid as an active ingredient.

16 Claims, 2 Drawing Sheets

OTHER PUBLICATIONS

Ledda-Columbano et al., "Induction of hepatocyte proliferation by retinoic acid," Carcinogenesis (Oxford), vol. 25, No. 11, Nov. 2004, pp. 2061-2066, XP002598452, ISSN: 0143-3334, Nov. 2004.
Extended European Search Report that issued with respect to European Patent Application No. 08764189.0, mailed Sep. 23, 2010.
Chinese Office Action issued in counterpart Chinese Application No. 20080021286.4, dated Dec. 3, 2012, and English Translation.
Japanese Office Action issued with respect to counterpart Japanese Application No. 2009-520336, dated Apr. 2, 2013, with English Translation thereof.
Tsurumi et al., "Differentiation induction of human promyelocytic leukemia cells by acyclic retinoid (polyprenoic acid)", International Journal of Hematology, No. 59, 1993, pp. 9-15.

* cited by examiner

[Fig. 1]
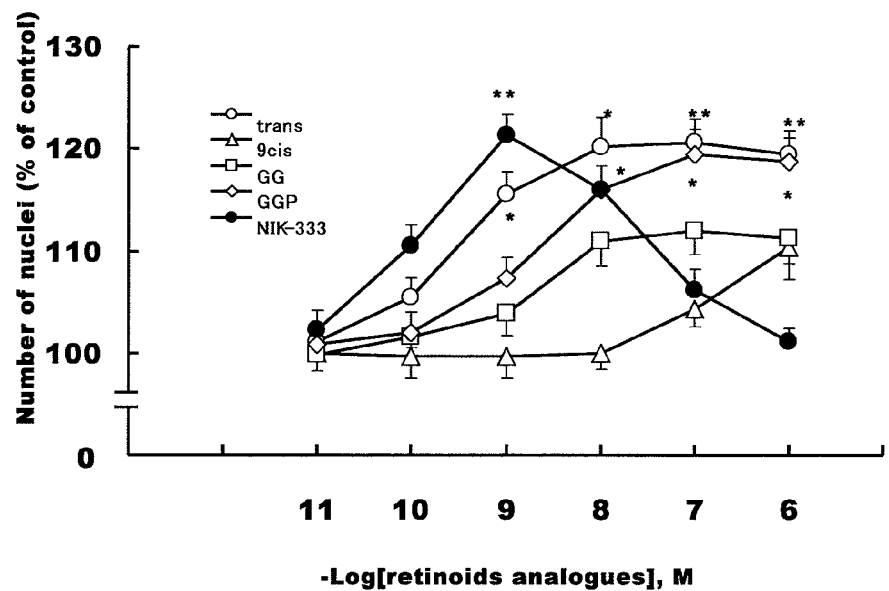
[Fig. 2]
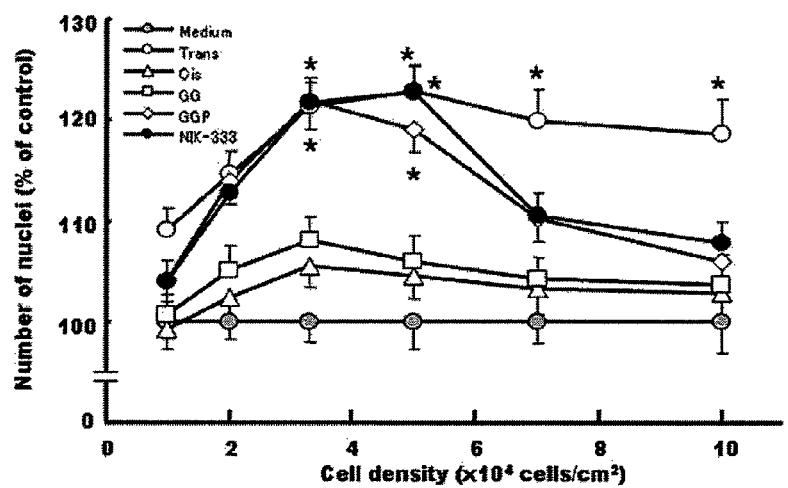

[Fig. 3]
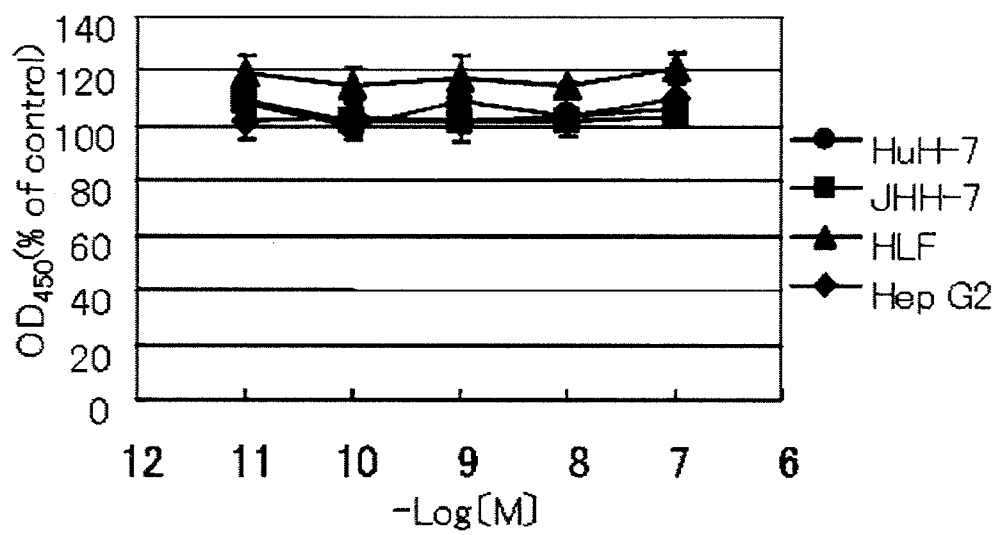
[Fig. 4]
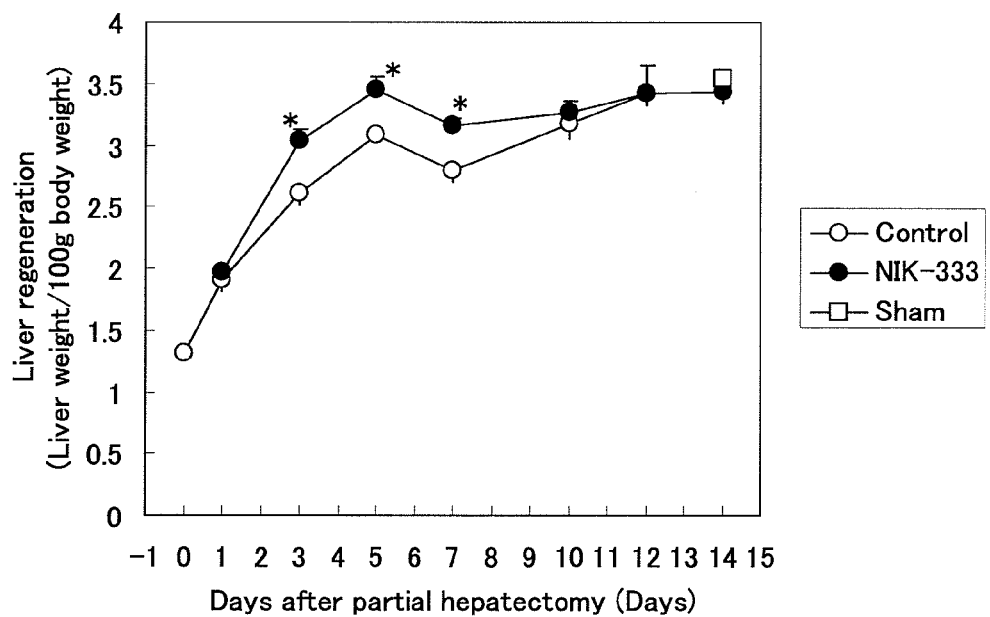

MEDICAMENT HAVING PROMOTING ACTION ON HEPATOCYTE PROLIFERATION

RELATED APPLICATIONS

The present application is a Divisional of U.S. application Ser. No. 12/665,342, which is a national stage of International Application No. PCT/JP2008/001606, filed Jun. 20, 2008, which claims priority to Japanese Patent Application No. 2007-163355, filed Jun. 21, 2007. The disclosures of application Ser. No. 12/665,342 and PCT/JP2008/001606 are expressly incorporated by reference herein in their entireties.

TECHNICAL FIELD

The present invention relates to a medicament comprising a polyprenyl compound having a promoting action on hepatocyte proliferation as an active ingredient and used for a liver regeneration therapy.

BACKGROUND ART

As liver regeneration therapy at present, glucagon-insulin therapy has been clinically used for fulminant hepatitis. However, effectiveness thereof is not satisfactory. Further, among hepatoma patients, hepatoma resection is not applied to those with complication of chronic hepatitis or cirrhosis showing decrease of hepatic residual function, because sufficient liver regeneration cannot be expected after the resection and a problem of hepatic failure may arise. Under the background circumstances, it is strongly desired to develop a medicament having a promoting action on liver regeneration which is safely usable for prophylactic and/or therapeutic treatment of fulminant hepatitis or hepatic failure after hepatoma resection. As agents for promoting liver regeneration in a level of fundamental experiment, growth factors such as hepatocyte growth factor, transforming growth factor-$\alpha$ and epidermal growth factor, amino acids such as valine, leucine, alanine and glutamine, thrombocyte, thrombopoietin, anti-kallikrein antibodies, and the like have been reported (Non-patent documents 1 to 5, Patent documents 1 to 5).

In particular, hepatoma is a disease associated with poor prognosis, and it is known that the disease recurs at a high rate even after treatment. For example, it is impossible to use a substance as a medicament that induces transformation of hepatocytes or a substance having proliferation promoting action on cancer cells, even if said substance has promoting action on hepatocyte proliferation, because the substance may promote recurrence of hepatoma. Therefore, in order to improve treatment results of hepatoma and prevent recurrence thereof over a long period of time, it is an important subject to develop a medicament that suppresses oncogenesis in the liver and promotes liver regeneration.

As substances that suppress oncogenesis in the liver, retinoids such as all-trans-retinoic acid (ATRA), 9-cis-retinoic acid (9CRA), and fenretinide are reported, and among them, ATRA is reported to induce the proliferation of mouse hepatocytes. However, ATRA is also reported to promote oncogenesis in a mouse liver carcinogenic model, and therefore safety of ATRA is questioned. Further, it is also known that administration of ATRA induces serious side reactions such as retinoic acid syndrome (various symptoms including pyrexia, dyspnoea, retention of pleural effusion, lung infiltration, interstitial pneumonia, pulmonary congestion, hypoxemia, hypotension, hepatic failure, renal failure, and multiple organ failure), and leukocytosis. Therefore, at present, any safe substance that suppresses liver oncogenesis and promotes proliferation of hepatocytes has not yet been known.

One of polyprenyl compounds, (2E,4E,6E,10E)-3,7,11,15-tetramethyl-2,4,6,10,14-hexadecapentaenoic acid (hereinafter in the specification, this substance may also be referred to as "NIK-333") is known to have affinity to retinoic acid-binding proteins and retinoic acid receptors, and have differentiation inducing action and apoptosis inducing action for hepatoma cells. Recurrence of hepatoma after radical cure was significantly suppressed by long-term administration of NIK-333 over one year, and thus hepatoma recurrence suppressing action of NIK-333 has been confirmed (Non-patent document 6). However, it has been absolutely not known so far that polyprenyl compounds promote proliferation of hepatocytes. In addition, it has been reported that NIK-333 does not affect proliferation of primarily cultured mouse hepatocytes at a concentration inducing apoptosis of hepatoma cells (Non-patent documents 7 and 8), and it has also been reported that NIK-333 delays DNA synthesis of a regenerated liver in a rat partially hepatectomized model (Non-patent document 9).

Non-patent document 1: Biohem. Biophys. Res. Commun., 133, pp. 1042-1050, 1985
Non-patent document 2: Proc. Natl. Acad. Sci. USA, 86, pp. 1558-1562, 1989
Non-patent document 3: Cell, 18, pp. 153-163, 1979
Non-patent document 4: Eur. J. Pharmacol., 510, pp. 167-180, 2005
Non-patent document 5: Kanzo (Liver, Journal of the Japan Society of Hepatology, 44, pp. 383-394, 2003
Non-patent document 6: N. Eng. J. Med., 334, pp. 1561-1567, 1996
Non-patent document 7: Biohem. Biophys. Res. Commun., 219, pp. 100-104, 1996
Non-patent document 8: J. Lipid Res., 45, pp. 1092-1103, 2004
Non-patent document 9: Kanzo, 26, pp. 605-612, 1985
Patent document 1: Japanese Patent Unexamined Publication (KOKAI) No. 8-67628
Patent document 2: Japanese Patent Unexamined Publication No. 5-229940
Patent document 3: Japanese Patent Unexamined Publication No. 2007-23002
Patent document 4: Japanese Patent Unexamined Publication No. 2007-45721
Patent document 5: Japanese Patent Unexamined Publication No. 2003-252792

DISCLOSURE OF THE INVENTION

Object to be Achieved by the Invention

An object of the present invention is to provide a medicament for promoting liver regeneration which has a promoting action on hepatocyte proliferation and is useful for therapeutic and/or prophylactic treatment of hepatic failure, and the like. A particularly preferred object of the present invention is to provide the aforementioned medicament having both of a promoting action on hepatocyte proliferation and a liver oncogenesis suppressing action as a medicament useful for prophylactic and therapeutic treatments of hepatoma.

Means for Achieving the Object

The inventors of the present invention conducted various researches to find a substance having a promoting action on hepatocyte proliferation and useful as a medicament for promotion of liver regeneration. As a result, they found that polyprenyl compounds, which was reported to have a liver oncogenesis suppressing action, promoted the proliferation of primarily cultured rat hepatocytes at a low concentration not affecting proliferation of hepatoma cells, and that the proliferated cells maintained cell density dependency, namely, the cells were non-transformation-induced cells (non-hepatoma cells), indicating that polyprenyl compounds selectively promoted the proliferation of normal hepatocytes. The present invention was accomplished on the basis of the aforementioned findings.

The present invention thus provides a medicament for promoting proliferation of hepatocytes, which comprises a polyprenyl compound as an active ingredient. The present invention also provides a medicament for promoting regeneration of liver, which comprises a polyprenyl compound as an active ingredient. As preferred embodiments thereof, the aforementioned medicament, which is used for promotion of liver regeneration in a therapeutic treatment of hepatoma, and the aforementioned medicament, which is used for promotion of liver regeneration after resection of hepatoma are provided.

According to preferred embodiments of the aforementioned invention, there are provided the aforementioned medicaments, wherein the polyprenyl compound is a polyprenylcarboxylic acid; the aforementioned medicaments, wherein the polyprenylcarboxylic acid is 3,7,11,15-tetramethyl-2,4,6,10,14-hexadecapentaenoic acid; and the aforementioned medicaments, wherein the polyprenylcarboxylic acid is (2E,4E,6E,10E)-3,7,11,15-tetramethyl-2,4,6,10,14-hexadecapentaenoic acid.

From other aspects of the present invention, there are provided use of a polyprenyl compound, preferably a polyprenylcarboxylic acid, more preferably 3,7,11,15-tetramethyl-2,4,6,10,14-hexadecapentaenoic acid, particularly preferably (2E,4E,6E,10E)-3,7,11,15-tetramethyl-2,4,6,10,14-hexadecapentaenoic acid, for manufacture of the aforementioned medicaments; a method for promoting proliferation of hepatocytes, which comprises the step of administering an effective amount of a polyprenyl compound to a mammal including human in need of promotion of proliferation of hepatocytes; and a method for promoting liver regeneration, preferably promoting liver regeneration in therapeutic treatment of hepatoma, which comprises the step of administering an effective amount of a polyprenyl compound to a mammal including human in need of regeneration of liver.

BRIEF DESCRIPTION OF THE DRAWINGS

FIG. 1 is a graph showing action of retinoids and polyprenyl compounds for promoting proliferation of primarily cultured rat hepatocytes. Meanings of the abbreviations used in the graph are as follows: NIK-333: (2E,4E,6E,10E)-3,7,11,15-tetramethyl-2,4,6,10,14-hexadecapentaenoic acid, trans: all-trans-retinoic acid, cis: 9-cis-retinoic acid, GG: geranylgeraniol, and GGP: geranylgeranyl pyrophosphate ammonium salt, and "*" and "**" indicate that there is significant difference (P<0.05 or P<0.01, respectively) compared with the control group in which the solvent was added.

FIG. 2 is a graph showing cell density dependency with the action of retinoids and polyprenyl compounds for promoting proliferation of primarily cultured rat hepatocytes. The abbreviations used in the graph have the same meanings as those of FIG. 1, and "*" indicates that there is significant difference (P<0.05) compared with the control group in which the solvent was added.

FIG. 3 is a graph showing that NIK-333 have no promoting action on the proliferation of a cell line derived from human hepatic cancer at a concentration showing the action of promoting proliferation of primarily cultured rat hepatocytes.

FIG. 4 is a graph showing effect of NIK-333 for promoting liver regeneration in a partially hepatectomized liver regeneration model animal. The values are indicated as average±standard error in the graph, and "*" indicates that there is significant difference (P<0.05).

BEST MODE FOR CARRYING OUT THE INVENTION

The medicament of the present invention is characterized to comprise a polyprenyl compound as an active ingredient, and to have an action of promoting proliferation of hepatocytes and an action of promoting liver regeneration.

Examples the polyprenyl compound as the active ingredient of the medicament of the present invention include, for example, 3,7,11,15-tetramethyl-2,4,6,10,14-hexadecapentaenoic acid, geranylgeranoic acid (GGA), phytanic acid, and the like, which are polyprenylcarboxylic acid, as well as polyprenylcarboxylic acid esters, vitamin K1, vitamin K2, and the like.

Although the polyprenyl compound used as the active ingredient of the medicament of the present invention may be a cyclic or acyclic polyprenyl compound, the compound is preferably an acyclic polyprenyl compound. The acyclic polyprenyl compound means a compound containing several straight chain isoprene units. Type of the functional group at the end of the acyclic polyprenyl compound is not particularly limited. Examples include polyprenyl alcohols (polyprenols) having a primary allylic hydroxyl group at the end, compounds consisting of a polyprenol of which end hydroxyl group forms an ester with an organic acid, polyprenylcarboxylic acids having carboxyl group at the end, and the like, but not limited to these examples. Polyprenylcarboxylic acids can be preferably used.

Preferred polyprenylcarboxylic acids include, for example, 3,7,11,15-tetramethyl-2,4,6,10,14-hexadecapentaenoic acid, and more preferred polyprenyl carboxylic acids include (2E,4E,6E,10E)-3,7,11,15-tetramethyl-2,4,6,10,14-hexadecapentaenoic acid (NIK-333). The polyprenyl compounds used in the present invention can be synthesized by known methods (Japanese Patent Publication (KOKOKU) No. 63-32058, J. Chem. Soc. (C), p. 2154, 1966, and the like).

As the polyprenyl compound, a physiologically acceptable salt thereof may be used. Type of the salt is not particularly limited, and it may be an acid addition salt or base addition salt. A hydrate or solvate of a polyprenyl compound in a free form or in the form of a salt may also be used. The term "polyprenyl compound" used in this specification encompasses salts, hydrates, solvates, and the like, as well as arbitrary stereoisomers (including enantiomers and diastereoisomers), mixtures of stereoisomers, arbitrary geometrical isomers, arbitrary mixtures of geometrical isomers, and the like.

The medicament provided by the present invention has a promoting action on hepatocyte proliferation, and also has a promoting action on liver regeneration based on the promoting action on hepatocyte proliferation. Therefore, the medicament of the present invention can achieve, for example, promotion of the regeneration of the liver on the basis of the promotion on the proliferation of normal hepatocytes in hepatic diseases such as hepatic failure or hepatoma, and thereby therapeutic treatments of the liver diseases can be efficiently attained. Moreover, the medicament of the present invention can also be used from a preventive viewpoint, for example, for prevention of recurrence of a hepatic disease by attaining normalization of the liver on the basis of the liver regeneration. The hepatic disease as a target of application of the medicament of the present invention is not particularly limited. Examples include viral or alcoholic acute or chronic hepatitis, fulminant hepatitis, cirrhosis, hepatic failure, hepatoma, and the like, but not limited to these examples.

Polyprenyl compounds are known to have an apoptosis inducing action for hepatoma cells, and it has been reported that NIK-333 does not affect proliferation of hepatocytes at a concentration inducing the apoptosis (Non-patent documents 7 and 8). Although it is not intended to be bound by any specific theory, the promoting action on hepatocyte proliferation of the polyprenyl compounds of the present invention is exhibited at a concentration lower than the concentration at which the apoptosis of hepatoma cells is induced. Specifically, although the polyprenyl compounds, of which typical example is NIK-333, exhibit a proliferation promotion action for normal hepatocytes to selectively proliferate normal hepatocytes at a low concentration, and selectively induce apoptosis of hepatoma cells at a high concentration to exhibit an anticancer action. Therefore, especially in the therapeutic treatment of hepatoma, if the medicament of the present invention is administered to a patient after resection of hepatoma, the medicament can induce apoptosis of hepatoma cells when a high blood concentration thereof is maintained immediately after the administration, and can exhibit a proliferation promotion action for normal hepatocytes when a low blood concentration thereof is obtained several hours after the administration, and therefore the medicament can be used as an extremely safe and effective medicament. Further, by suitably choosing high concentration administration or low concentration administration depending on the therapeutic stage, for example, high concentration administration can be maintained immediately after resection of hepatoma to eradicate hepatoma cells, and low concentration administration can be maintained to promote liver regeneration during the following convalescence period.

The medicament of the present invention can usually be prepared as a pharmaceutical composition comprising a polyprenyl compound, and administered by an appropriate administration method of oral administration or parenteral administration. Examples of forms of the pharmaceutical composition suitable for oral administration include, for example, tablets, granules, capsules, soft capsules, pills, powders, solutions, and the like. Examples of forms of the pharmaceutical composition for parenteral administration include, for example, injections, suppositories, and the like. These pharmaceutical compositions can be prepared by a conventional method using a polyprenyl compound or a pharmacologically acceptable salt thereof and one or more kinds of usual pharmaceutical carriers.

For example, in the case of medicament suitable for oral administration, a desired pharmaceutical composition can be prepared by using, as pharmaceutical carriers, excipients such as lactose, glucose, corn starch and sucrose, disintegrating agents such as carboxymethylcellulose calcium and hydroxypropylcellulose, lubricants such as calcium stearate, magnesium stearate, talc, polyethylene glycol and hydrogenated oil, binders such as hydroxypropylcellulose, hydroxypropylmethylcellulose, carboxymethylcellulose, polyvinyl alcohol, gelatin and gum arabic, and moistening agents such as glycerin and ethylene glycol, as well as surfactants, flavoring agents and the like as required.

Further, in the case of medicament suitable for parenteral administration, there can be used, as pharmaceutical carriers, diluents such as water, ethanol, glycerin, propylene glycol, polyethylene glycol, vegetable oil, agar and tragacanth gum as well as dissolving aids, suspending agents, emulsifiers, stabilizers, buffers, isotonic agents, preservatives, soothing agents and the like as required.

Although dose of the medicament of the present invention is not particularly limited, for example, it may be, for an adult, 50 to 1,200 mg, preferably 300 to 900 mg, per day in the case of oral administration, or 1 to 1,200 mg, preferably 5 to 900 mg, per day in the case of parenteral administration. Desired promoting effects can be expected by administering the compound at a dose within the aforementioned range 1 to 3 times per day as the whole amount or divided amounts.

EXAMPLES

The present invention will be explained more specifically with reference to examples. However, the scope of the present invention is not limited by these examples.

Example 1

Effect of Promoting Proliferation of Primarily Cultured Rat Hepatocytes

Wistar male rats (weight: 200 to 205 g) were used, and hepatocytes were isolated by the in situ collagenase perfusion technique according to the method of Seglen et al. (Methods. Cell Biol., 13, pp. 29-83, 1975). The isolated hepatocytes were suspended in the Williams' medium E (containing 0.1 µg/mL aprotinin, 100 U/mL of penicillin G, 0.1 mg/mL of streptomycin, and 0.1 nmol/L of dexamethasone) containing 5% bovine neonate serum 3 times for washing, and then inoculated on a collagen coated culture dish (35 mm Φ) at a cell density of $3.3 \times 10^4$ cells/cm$^2$. The cells were adhered to the culture dish by culturing them at 37° C. for 3 hours in the presence of 5% $CO_2$ to prepare a primarily cultured hepatocyte cell line. Survival rate of the isolated hepatocytes was obtained by the trypan blue exclusion method, and those showing a survival rate not lower than 93% were used for the following experiments.

The medium of the isolated hepatocytes was replaced with serum-free Williams' medium E (containing 0.1 µg/mL of aprotinin, 100 U/mL of penicillin G, 0.1 mg/mL of streptomycin), and (2E,4E,6E,10E)-3,7,11,15-tetramethyl-2,4,6,10,14-hexadecapentaenoic acid (NIK-333), all-trans retinoic acid (trans), 9-cis-retinoic acid (cis), geranylgeraniol (GG) and geranylgeranyl pyrophosphate ammonium salt (GGP) were each added at final concentrations of $10^{-11}$, $10^{-10}$, $10^{-9}$, $10^{-8}$, $10^{-7}$, and $10^{-8}$ mol/L. As the solvent, a phosphate buffer (PBS, pH 7.4) containing 0.01% DMSO was used. Four hours after the addition of the agents, number of nuclei was measured as follows. The hepatocytes were washed with PBS, and then added with 0.25 mL of a 0.1 mol/L citric acid solution containing 0.1% Triton X-100. The cells were incubated at 37° C. for 30 minutes to solubilize the cell membranes and thereby obtain naked nuclei. The same volume of a PBS solution containing 0.3% trypan blue was further added, and number of the stained nuclei was measured with a hemacytometer. As shown in FIG. 1, significant effect of promoting proliferation of the primarily cultured rat hepatocytes was observed for NIK-333, trans, and GGP, and NIK-333 gave the strongest effect.

Example 2

Influence on Cell Density-Dependent Proliferation of Primarily Cultured Rat Hepatocytes Hepatocytes isolated by the same method as that of Example 1 were inoculated at cell densities of 1, 2, 3.3, 5, 7, and 10×10⁴ cells/cm². NIK-333 ($10^{-9}$ mol/L), trans ($10^{-7}$ mol/L), cis ($10^{-6}$ mol/L), GG ($10^{-7}$ mol/L), and GGP ($10^{-6}$ mol/L) were each added to the hepatocytes pre-cultured in the same manner as that of Example 1. Four hours after the addition of the agents, number of nuclei was measured by the same method as that of Example 1. As shown in FIG. 2, trans gave the cell proliferation promoting action even when the cell density was increased, and thus action of inducing transformation of hepatocytes was suggested. Whilst, the cell proliferation promoting action of NIK-333 and GGP was decreased with the increase of the cell density, and it was suggested that the cells were maintained to be in normal forms.

Example 3

Influence on Proliferation of Cells of Cell Line Derived from Human Hepatoma

Cells of cell lines derived from human hepatoma (HuH-7, JHH-7, HLF, Hep G2) were cultured by using a minimum essential medium (MEM) (100 U/mL of penicillin G, 0.1 mg/mL of streptomycin) containing 5% bovine neonate serum. The cells were inoculated on a 96-well plate at a cell density of 1×10⁴ cells/mL, and cultured overnight at 37° C. in the presence of 5% $CO_2$. The medium was exchanged for a 1% serum containing MEM (100 U/mL of penicillin G, 0.1 mg/mL of streptomycin), and NIK-333 was added at final concentrations of $10^{-11}$, $10^{-10}$, $10^{-9}$, $10^{-8}$, and $10^{-7}$ mol/L. As the solvent, DMSO was used. The cells were cultured overnight at 37° C. in the presence of 5% $CO_2$, and live cell count was measured. The live cell count was measured by using Cell Counting Kit (Wako Pure Chemical Industries). A WST-1 solution was added to each well in a volume of 10 μL, and the culture was incubated at 37° C. for 3 hours in the presence of 5% $CO_2$. Absorbance was measured for each well at a measurement wavelength of 450 nm and a reference wavelength of 655 nm using a microplate reader. As shown in FIG. 3, NIK-333 gave no proliferation promotion action for any of the four kinds of cell strains derived from human hepatoma.

Example 4

Liver Regeneration Promoting Effect of NIK-333 in Partially Resected Liver Regeneration Model Animal Hepatocyte proliferation promoting effect of NIK-333 was examined by using a 70% partially hepatectomized rat (partial hepatectomy: PH rat) as an in vivo experiment system. Wistar male rats (weight: 130 to 170 g) were subjected to 70% partial hepatectomy according to the method of Higgins G. M. et al. (Arch. Pathol., 12, pp. 186-202, 1931) to prepare PH rats. NIK-333 (solvent was soybean oil, 0.4 mg/kg/day) was orally administered to these PH rats once per day, the administration was repeated and continued for 1 to 14 days, and reaction was observed over time. The model animals fed for 1 to 14 days after the hepatectomy were subjected to abdominal section under diethyl ether anesthesia, and the remaining livers were extracted. The remaining livers were separated into normal hepatic tissues and necrotizing hepatic tissues (liver tissues which were not excisable by the partial hepatectomy and remained), and weight of each was measured (wet weight). The examination was performed for three animals for each group, and the results are indicated as average±standard error. Student t-test was performed between a solvent administered group (soybean oil, 4 mL/kg, p.o.) as a control group and the NIK-333 administered group. The significance level of the test was set at 5% and 1% on both sides.

In the NIK-333 administered group (0.4 mg/kg/day), earlier recovery of liver weight was observed compared with the control group. The most remarkable difference was observed 3 days after PH. At that time, the liver weight of the control group was 2.5 g liver weight/100 g body weight (LW/BW) (increase rate was about 70%), the liver weight of the NIK-333 administered group was 3.0 g LW/BW (increase rate was 85%), and thus significant difference was observed between both the groups. The results are shown in FIG. 4 (the values in the graph are indicated as average standard error, and * indicates that there is significant difference with P<0.05). Thus, in the NIK-333 administered group, enhancement in the proliferation stage from the 3rd day after the operation was remarkable, and further proliferation was observed even on the 5th day after PH, but hyperproliferation exceeding the value of the Sham group was not observed on the 14th day. From the results explained above, it was verified that NIK-333 exhibited an action of promoting proliferation of normal hepatocytes as shown by the in vitro experiment system (primarily cultured hepatocyte system) at an early stage, and also promoted liver regeneration without resulting hyperproliferation.

INDUSTRIAL APPLICABILITY

The medicament provided by the present invention has promoting action on liver regeneration based on promoting action on hepatocyte proliferation, and can selectively proliferate normal hepatocytes. Therefore, the medicament is useful for liver regeneration, for example, in therapeutic treatment of hepatoma, and the like.

What is claimed is:

1. A method for promoting proliferation of hepatocytes, comprising administering to a mammal in need thereof a composition to promote proliferation of hepatocytes, the composition comprising as an active ingredient 3,7,11,15-tetramethyl-2,4,6,10,14-hexadecapentaenoic acid in an amount effective so that the 3,7,11,15-tetramethyl-2,4,6,10,14-hexadecapentaenoic acid induces proliferation of hepatocytes and does not induce proliferation of hepatoma.

2. The method according to claim 1, wherein the 3,7,11,15-tetramethyl-2,4,6,10,14-hexadecapentaenoic acid comprises (2E,4E,6E,10E)-3,7,11,15-tetramethyl-2,4,6,10,14-hexadecapentaenoic acid.

3. The method according to claim 1, wherein the promoting proliferation of hepatocytes comprises promoting liver regeneration.

4. The method according to claim 3, wherein the promoting liver regeneration comprises promoting liver regeneration in therapeutic treatment of hepatoma.

5. The method according to claim 4, wherein the therapeutic treatment of hepatoma includes resection of hepatoma, and the administration of the composition comprises administration of the composition after the resection of hepatoma.

6. The method according to claim 1, wherein the mammal is a human.

7. The method according to claim 3, wherein the mammal is a human.

8. The method according to claim 4, wherein the mammal is a human.

9. The method according to claim 5, wherein the mammal is a human.

10. The method according to claim 2, wherein the promoting proliferation of hepatocytes comprises promoting liver regeneration.

11. The method according to claim 10, wherein the promoting liver regeneration comprises promoting liver regeneration in therapeutic treatment of hepatoma.

12. The method according to claim 11, wherein the therapeutic treatment of hepatoma includes resection of hepatoma, and the administration of the composition comprises administration of the composition after the resection of hepatoma.

13. The method according to claim 2, wherein the mammal is a human.

14. The method according to claim 10, wherein the mammal is a human.

15. The method according to claim 11, wherein the mammal is a human.

16. The method according to claim 12, wherein the mammal is a human.

* * * * *